United States Patent
Taninaka et al.

(10) Patent No.: US 8,012,417 B2
(45) Date of Patent: Sep. 6, 2011

(54) SOLUTION DISCHARGING METHOD AND SOLUTION DISCHARGING DEVICE

(75) Inventors: Kiyoshi Taninaka, Kawasaki (JP); Jun Sasaki, Kawasaki (JP); Akihiko Yabuki, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 1159 days.

(21) Appl. No.: 11/797,630

(22) Filed: May 4, 2007

(65) Prior Publication Data
US 2007/0264162 A1 Nov. 15, 2007

(30) Foreign Application Priority Data
May 12, 2006 (JP) .................. 2006-133512

(51) Int. Cl.
*B01L 3/02* (2006.01)

(52) U.S. Cl. .......... 422/62; 422/400; 137/825; 137/832

(58) Field of Classification Search .......... None
See application file for complete search history.

(56) References Cited

U.S. PATENT DOCUMENTS

| | | | |
|---|---|---|---|
| 4,532,205 A * | 7/1985 | Ansorge ..................... | 435/30 |
| 5,225,750 A | 7/1993 | Higuchi et al. | |
| 5,456,880 A * | 10/1995 | Miura ........................ | 422/509 |
| 2003/0070710 A1 * | 4/2003 | Inayama et al. ............. | 137/85 |
| 2003/0220585 A1 * | 11/2003 | Hissong ...................... | 600/560 |

FOREIGN PATENT DOCUMENTS

| | | |
|---|---|---|
| DE | 44 01 076 | 7/1995 |
| GB | 2 114 740 | 8/1983 |
| JP | 4-304881 | 10/1992 |
| JP | 2004-166653 | 6/2004 |
| WO | 93/07256 | 4/1993 |

OTHER PUBLICATIONS

European Search Report issued in corresponding European Patent Application No. 07105503.2 dated Jul. 26, 2007 (7 pages).

* cited by examiner

*Primary Examiner* — In Suk Bullock
*Assistant Examiner* — Timothy G Kingan
(74) *Attorney, Agent, or Firm* — Fujitsu Patent Center

(57) ABSTRACT

A microinjection device includes a pressure pump and a regulator that is connected to the pressure pump and that maintains constant pressure. A regulating chamber is connected to the regulator and an internal pressure of the regulating chamber is maintained to a predetermined pressure. A valve is connected to the regulating chamber and a hollow capillary is connected to the valve. An operator opens/closes the valve in the process of injecting material in a cell.

4 Claims, 6 Drawing Sheets

SOLUTION DISCHARGING METHOD AND SOLUTION DISCHARGING DEVICE

CROSS REFERENCE TO RELATED APPLICATION

This application claims the benefit under 35 U.S.C. Section 119, of Japanese Patent Application No. 2006-133512, filed May 12, 2006, which is hereby incorporated by reference in its entirety into this application.

BACKGROUND OF THE INVENTION

1. Field of the Invention

The present invention generally relates to injecting material in the cells by using air pressure.

2. Description of the Related Art

In the field of new drug designing, a microinjection device is used for injecting a solution (usually a medicinal solution) into a cell. FIG. 6 is an example of a conventional device. As shown in the diagram, reference numeral 1 denotes a positive pressure pump, and reference numeral 2 denotes a negative pressure pump. Reference numeral 3 denotes a regulator that is connected to the positive pressure pump 1 and the negative pressure pump 2 for keeping constant the internal pressures thereof.

Reference numeral 4 denotes a capillary that discharges a solution into a cell due to the pressure from the regulator 3. The capillary 4 is similar to an injection syringe, and has a fine needle at its tip. The internal diameter of the tip is 0.5 µm and the external diameter is 1 µm. Reference numeral 6 denotes a tube that transmits the pressure from the regulator 3 to the capillary 4, and reference numeral 5 denotes a pressure sensor which is located in the middle of the tube 6.

The pressure detected by the pressure sensor 5 is output to the regulator 3, and the regulator 3 adjusts the internal pressure so that the pressure detected by the pressure sensor 5 is maintained constant. Otherwise, it is possible to arrange the pressure sensor inside the regulator 3 and adjust the internal pressure so as to maintain constant output from the pressure sensor. Electric voltage is input to the regulator 3 as a control signal, and the regulator 3 generates a pressure that is proportional to the input electric voltage.

The needle attached to the tip of the capillary 4 is filled with the solution. Pressure applied by the regulator 3 thrusts a cylinder of the capillary 4 whereby the solution is discharged (injected) into the cell. The cell is observed for a change that occurs after injection of the solution. When the pressure inside the regulator 3 is to be brought back to the atmospheric pressure, air is pulled out from the regulator 3 by the negative pressure pump 2 whereby the pressure inside the regulator 3 is quickly brought back to the atmospheric pressure.

FIG. 7 depicts a pressure response curve of the conventional device. A horizontal axis indicates time and a vertical axis indicates pressure. Initially, the pressure is maintained to reverse flow preventing pressure. After time T1 is elapsed, the pressure reaches up to an injection pressure, and the capillary 4 injects the solution into the cell. The state that the capillary 4 is injected into the cell continues for a predetermined period after which the pressure lowers gradually. The injecting operation stops when the pressure reaches the reverse flow preventing pressure.

The conventional device can be used in a gene delivery device. In the gene delivery device, cells that flow through a micro fluid channel are observed by using a cell observing device, cells are trapped one by one with a cell trapping device, and genetic material and medicinal solutions are discharged into the cells by using a gene delivering micro needle (for example, see Japanese Patent Application Laid-Open No. 2004-166653). Furthermore, a microinjection apparatus has, at its tip, a micro instrument that is connected to a micro syringe, which is filled with the solution. When a male screw is rotated to move a plunger, into the micro syringe, the solution is discharged from the micro instrument (for example, see Japanese Patent Application Laid-Open No. H03-119989).

A microinjecting method of the microinjection apparatus involves filling predetermined volume of a solution in an extra fine capillary, with a tip that is of µm order, injecting the solution into the cell by pressurizing the capillary, and observing the response. In this process, it is necessary to control sequentially switching of the pressure between a pressure necessary for discharging the solution in the cell and a pressure necessary for preventing reverse flow of the solution into the capillary.

However, the conventional microinjection device, which has the structure shown in FIG. 6, does not take into account the pressure transient response. Therefore, when trace quantity of solution of pl (picolitre) order is to be discharged through injections such as injections into animal cells, if the delivery time is lowered to less than 1 second for speeding a discharge cycle, the set pressure and the set time deviate from the actual response, and adjustment of discharging volume of the solution is difficult.

Therefore, on the conventional microinjection apparatus, an experienced operator would adjust the pressure and the time for applying the pressure while taking into account swelling of the cell when injecting the solution into the cell. However, in this method, it is unclear whether a constant amount of material is discharged into the cell.

SUMMARY OF THE INVENTION

It is an object of the present invention to at least partially solve the problems in the conventional technology.

According to an aspect of the present invention, a solution discharging method for discharging a solution, from a hollow capillary with a narrow tip that is filled with the solution, into a cell due to an action of air pressure, includes connecting a regulating chamber to the capillary by a valve; and regulating air in the regulating chamber at a predetermined pressure before opening and closing the valve so that regulated pressure has a rectangular waveform thereby controlling quantity of the solution that is to be injected from the capillary into the cell to be constant.

According to another aspect of the present invention, a microinjection device includes a pressure pump; a regulator that is connected to the pressure pump and that maintains constant pressure; a regulating chamber that is connected to the regulator and an internal pressure of which is maintained to a predetermined pressure; a valve that is connected to the regulating chamber; and a capillary that is connected to the valve and that is used to inject solution in a cell.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Figure 1:
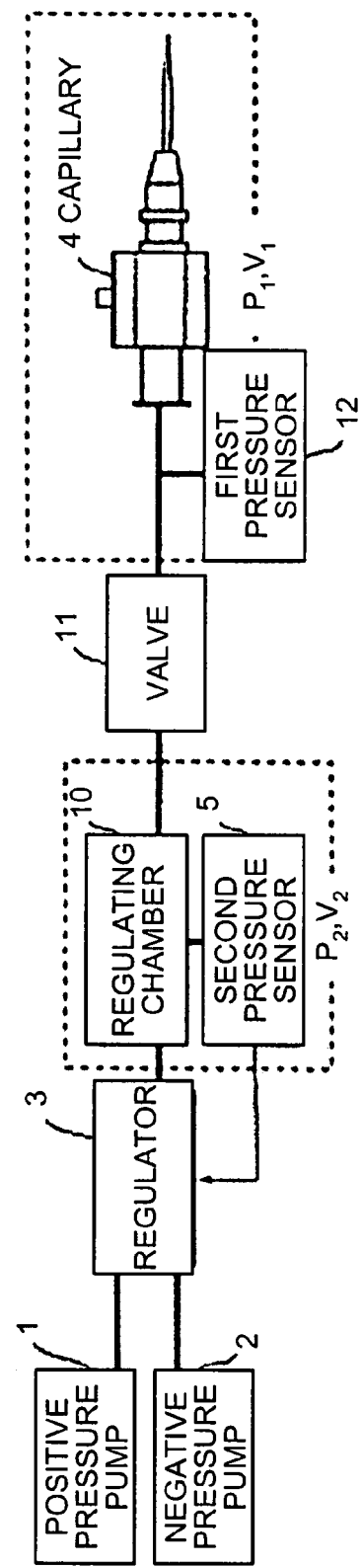
FIG. 1 is a schematic of a first embodiment according to the present invention.
Figure 6:
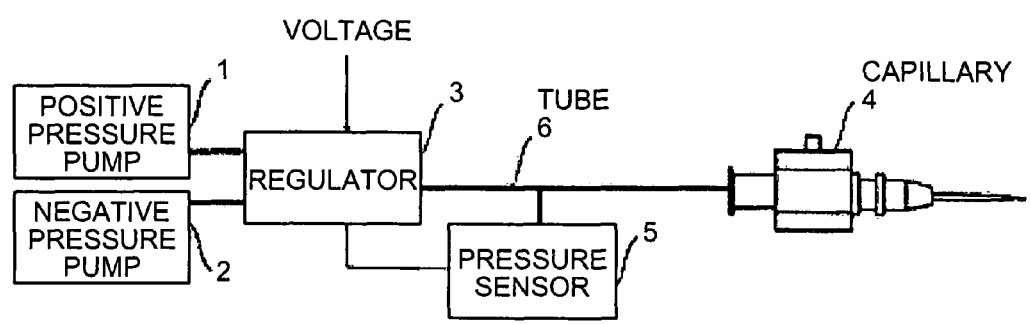
FIG. 6 is a schematic of an example of the structure of a conventional device.

Exemplary embodiments of the present invention are explained below in detail with reference to the accompanying drawings. FIG. 1 is a schematic of a first embodiment of the present invention. Components that are same as those shown in FIG. 6 are indicated with the same reference numerals. As shown in the diagram, reference numeral 1 denotes a positive pressure pump, and reference numeral 2 denotes a negative pressure pump. Reference numeral 3 denotes a regulator that regulates the pressure, reference numeral 10 denotes a regulating chamber that contains air whose pressure is regulated by the regulator 3. Reference numeral 5 denotes a second pressure sensor that detects pressure in the regulating chamber 10. The output of the second pressure sensor 5 is input in the regulator 3.

Pressure of air in the regulating chamber 10 is $P_2$ and volume is $V_2$. Reference numeral 4 denotes a capillary that injects solution into an animal cell and the like, reference numeral 11 denotes a valve arranged in between the regulating chamber 10 and the capillary 4. The valve 11, in which the material used is for example solenoid, is opened and closed to transmit air from the regulating chamber 10 to the capillary 4. Reference numeral 12 denotes a pressure sensor 1 that detects pressure of air in the capillary 4. The pressure of air inside the capillary 4 is $P_1$, and the volume is $V_1$. Operation of the apparatus, which has such configuration, is explained below.

At first, pressure of the regulating chamber 10 is set by the regulator 3 to a certain degree higher than the injection pressure. When an operator, while watching under a microscope, confirms that a needle of the capillary 4 reaches the cell, the operator opens the valve 11 to bring the pressure to injection pressure level. When the pressure reaches to the injection pressure level, the valve 11 is immediately closed. While the capillary 4 is discharging (injecting) the solution into the cell, the regulator 3 adjusts pressure in the regulating chamber 10 and sets it to lower level of than the reverse flow preventing pressure.

Afterwards, when the valve 11 is opened, pressure in the regulating chamber 10 and the capillary 4 becomes equal to the reverse flow preventing pressure, which prevents the solution from reverting into the capillary 4. The regulating chamber 10 is set to lower than the reverse flow preventing pressure in advance, which makes it possible to bring the level of the pressure entirely to the reverse flow preventing pressure, when the valve 11 is opened.

The relationship between the pressure before the opening of the valve and the pressure after the opening of the valve can be obtained through an equation of state of air. When P denotes pressure after the opening of the valve, $P_1$ denotes pressure in the capillary before the opening of the valve, $P_2$ denotes pressure in the regulator before the opening of the valve, $V_1$ denotes volume of air in the capillary, and $V_2$ denotes volume of air in the regulator, the pressure P after opening of the valve and volume ratio $\eta(=V_1/V_2)$ are represented with following equations:

$$P=(\eta P_1+P_2)/(\eta+1) \quad (1)$$

$$\eta=V_1/V_2=(P-P_2)/(P_1-P) \quad (2)$$

With the help of Equation 1, the pressure $P_2$ of the regulator before opening of the valve is represented with the following equation:

$$P_2=(\eta+1)P-\eta P_1 \quad (3)$$

$\eta$ can be calculated from Equation 2. Moreover, the pressure P after the opening of the valve is set in advance, the pressure $P_1$ in the capillary before the opening of the valve is known in advance from an output from the pressure sensor 12; therefore, it is possible to calculate the pressure $P_2$ of the regulator before the opening of the valve through Equation (3). When the pressure $P_2$ of the regulator before the opening of the valve is set to the value derived through Equation (3), the pressure at the time of opening of the valve 11 is regulated to the pressure P. That is, it is possible to maintain the pressure in the regulating chamber and the capillary.

Figure 2:
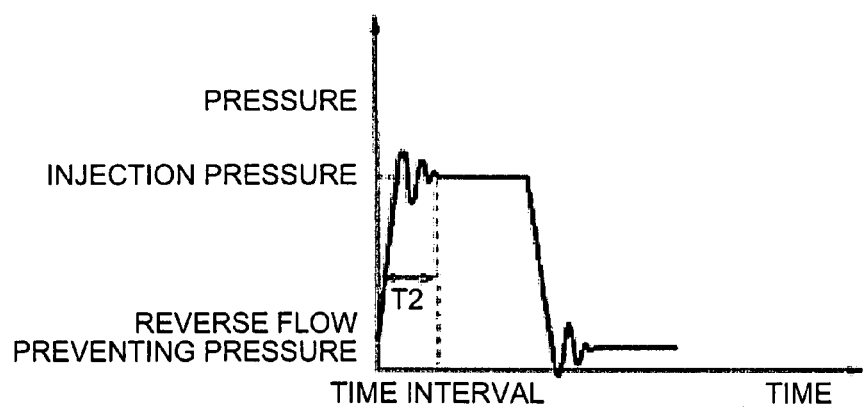
FIG. 2 is a graph for explaining a pressure response according to the present invention.
Figure 7:
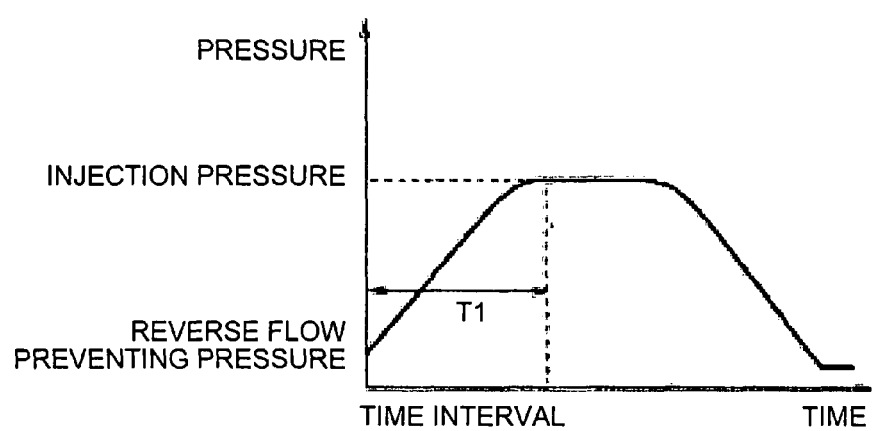
FIG. 7 is a graph for explaining a pressure response of the conventional device.

Pressure response in an ordinary microinjection device is as shown in FIG. 7. On the other hand, when the valve is switched from one state to another state in an instant, the pressure is transmitted at a sonic speed. The pressure response in such a case is as shown in a graph in FIG. 2. FIG. 2 is a graph for explaining the pressure response according to the present invention. The horizontal axis is time and the vertical axis is the pressure.

When the valve 11 is opened, the pressure rises from the reverse flow preventing pressure up to the injection pressure. Subsequently, when the valve 11 is closed, as shown in the diagram, the pressure drops to the reverse flow preventing pressure from the injection pressure in an instant. Rise and fall of the pressure is faster than the characteristic of the conventional device in FIG. 7.

As shown in the diagram, although some degree of transient response occurs due to reflection, time interval required for responding to regulation of the pressure to the injection pressure level is still shorter than the response as shown in FIG. 7. As shown FIG. 7 in the characteristic of the conventional device, the time required to attain target value is longer, whereas the transient response of the device in the present invention is only represented by vibrations near the target value. If the integration value of the vibrations is considered zero, it can be thought that the total quantity of injecting solution is proportional to a product of the target pressure and the time required for application of the pressure.

Thus, according to the first embodiment, a valve is arranged in between a regulating chamber and a capillary, and opened and closed to control the discharging quantity of solution from the capillary into a cell. That is, when the solution is injected into a cell, the quantity of solution can be easily controlled, and stable microinjection can be performed at high speed with less effect of transient response. According to the first embodiment, speedy rise of pressure in the capillary produces a rectangular waveform that depicts high degree of accuracy in time required for application of the pressure, high speed injection cycle, and improved accuracy of the quantity of the injecting solution.

Generally, the quantity of the injecting solution is proportional to pressure and time for which the pressure is applied; therefore, even if there is transient response, a method of controlling the quantity of the injecting solution according to the pressure time integration also has the same effect on the accuracy of the quantity of the injecting solution. That is, according to the present invention, because the integration value of the pressure applied to the capillary and the time for which the pressure is applied is controlled to a predetermined value, it is possible to always control the quantity of the injecting solution to a constant quantity.

Figure 3:
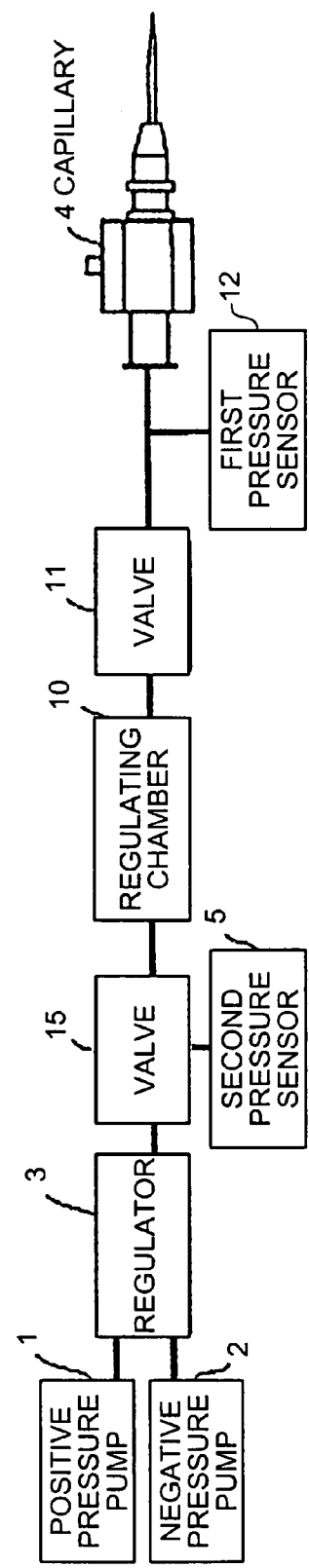
FIG. 3 is a schematic of a second embodiment according to the present invention.

FIG. 3 is a schematic of a second embodiment according to the present invention. Components that are same as those in FIG. 1 are indicated with the same reference numerals. The embodiment includes a second valve 15 in between the regulator 3 and the regulating chamber 10. Other aspects of the structure are same as shown in FIG. 1.

In such a structure when the first valve 11 is opened and closed, the second valve 15 is kept closed, which prevents pressure fluctuations from being conveyed to the regulator 3 and prevents occurrence of fluctuation in pressure.

Figure 4:
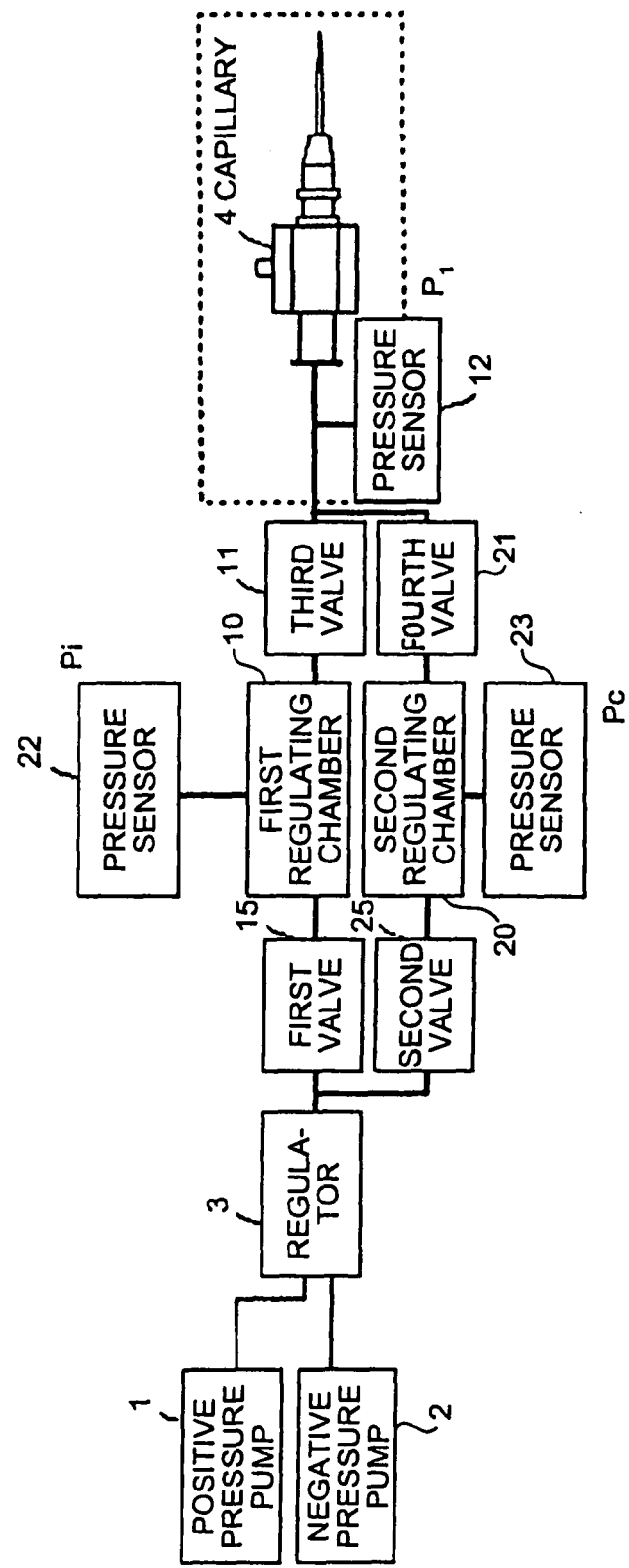
FIG. 4 is a schematic of a third embodiment according to the present invention.

FIG. 4 is a schematic of a third embodiment according to the present invention. Components that are same as those in FIG. 3 are indicated with the same reference numerals. In the diagram, reference numeral 25 denotes a second valve, which is connected to the regulator 3; reference numeral 20 denotes a second regulating chamber connected to the second valve; and reference numeral 21 denotes a fourth valve that is connected to the second regulating chamber. Reference numeral 22 denotes a pressure sensor that detects a pressure Pi in the first regulating chamber, and reference numeral 23 denotes a pressure sensor that detects a pressure Pc in the second regulating chamber. Reference numeral 12 denotes a pressure sensor that detects the pressure in the capillary.

Reference numeral 15 denotes the first valve, reference numeral 10 denotes the first regulating chamber connected to the first valve, and reference numeral 11 denotes a third valve connected to the first regulating chamber. The first valve and the second valve are commonly connected to the regulator 3, and the third valve and the fourth valve are commonly connected to the capillary 4.

Thus, according to the third embodiment, there is provided a double system of the regulator units formed of valves regulators, and valves. In this structure, while the third valve is closed, and the capillary 4 is injecting the solution in the cell, there is no need to regulate the regulating chamber 10. That is, when one system is operating the capillary 4, another system regulates the regulating chamber, and when injection operation of the capillary 4 is completed, opening of the fourth valve leads to a faster regulation after the opening of the valve. Thus, according to the third embodiment, time required to switch valves from one state to another is shortened.

Figure 5:
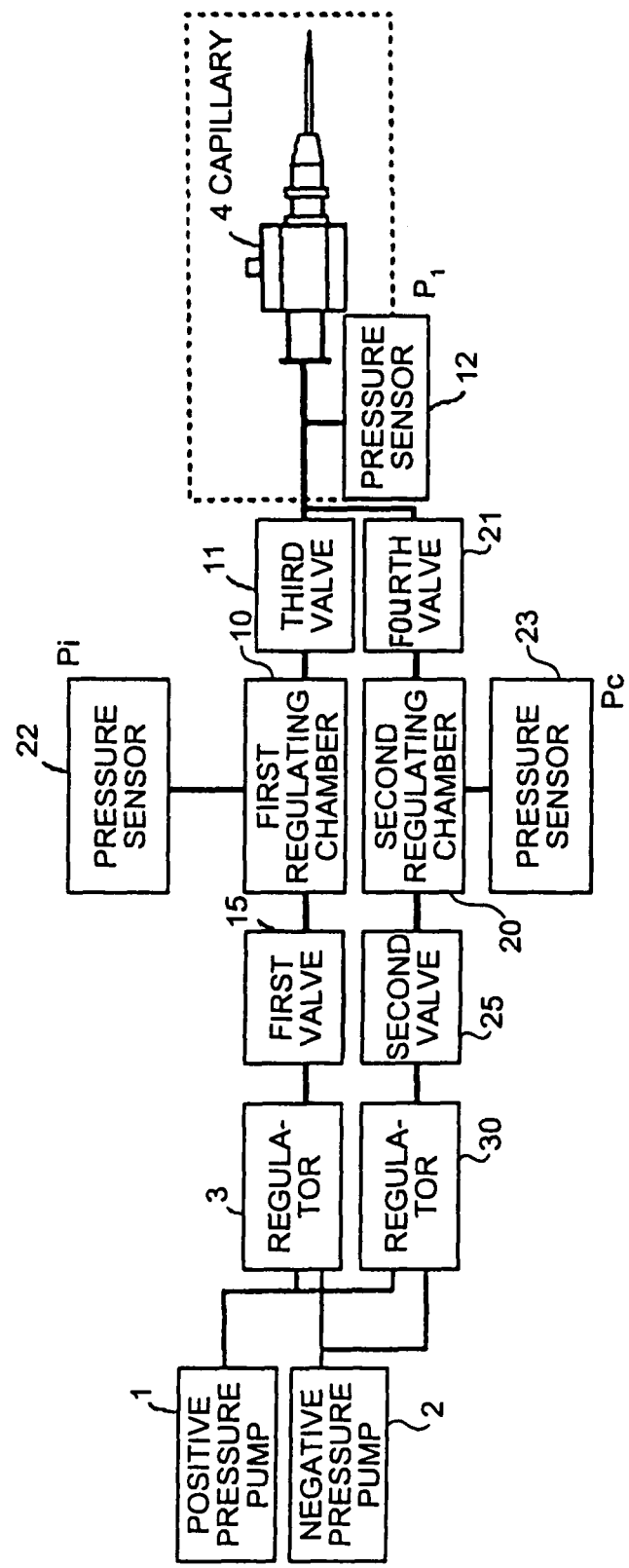
FIG. 5 is a schematic of a fourth embodiment according to the present invention.

FIG. 5 is a schematic of a fourth embodiment according to the present invention. Components that are same as those in FIG. 4 are indicated with the same reference numerals. The embodiment includes a second regulator 30 corresponding to the second regulation system shown in FIG. 4. The second regulator 30 is connected to the positive pump 1 and the negative pump 2, and is independent of a first regulator 3. The second regulator 30 is connected to the second valve. Remaining structure is the same as that shown in FIG. 4.

Such a structure allows the regulator 3 and a regulator 30 to adjust the air pressure in the regulator chamber independently, which allows the two systems to operate independently, and this structure operates faster than the one shown in FIG. 4.

Thus, according to an aspect of the present invention, high accuracy of time for which pressure is applied can be achieved due to fast rise in pressure response that creates rectangular waveform, and it is possible to have faster injection cycle and improve accuracy in quantity of discharging solution.

Although the invention has been described with respect to a specific embodiment for a complete and clear disclosure, the appended claims are not to be thus limited but are to be construed as embodying all modifications and alternative constructions that may occur to one skilled in the art that fairly fall within the basic teaching herein set forth.

What is claimed is:

1. A solution discharging method for discharging a solution, from a hollow capillary with a narrow tip that is filled with the solution, into a cell due to an action of air pressure, the solution discharging method comprising:
   connecting a regulating chamber to the capillary by a valve;
   detecting the air pressure in the capillary before opening the valve; and
   regulating air in the regulating chamber at a predetermined pressure before opening and closing the valve so that regulated pressure has a rectangular waveform thereby controlling quantity of the solution that is to be injected from the capillary into the cell to be constant, the predetermined pressure being based on the pressure detected by the detecting and an equation of state of air.

2. The solution discharging method according to claim 1, wherein an integration value of pressure applied to the capillary and time for which the pressure is applied is controlled to a predetermined value thereby controlling the quantity of the solution that is to be injected into the cell.

3. The solution discharging method according to claim 1, further comprising calculating the predetermined pressure based on the air pressure detected in the capillary and the equation of state of air, such that after opening the valve the air pressure in the capillary and regulating chamber is a predetermined value.

4. The solution discharging method according to claim 1, further comprising
   opening the valve after the air in the regulating chamber has been regulated to the predetermined pressure;
   closing the valve when the air pressure in the capillary reaches the injection pressure level;
   regulating the air pressure in the regulating chamber to a lower pressure than the pressure required to prevent reverse flow, whilst discharging the solution into the cell; and
   opening the valve after the air in the regulating chamber has been regulated to the lower pressure.

* * * * *